(12) United States Patent
Gleason et al.

(10) Patent No.: US 6,656,185 B2
(45) Date of Patent: Dec. 2, 2003

(54) TENSION BAND CLIP

(75) Inventors: Joseph E. Gleason, Eagan, MN (US); Francis Peterson, Prescott, WI (US)

(73) Assignee: Spineology Inc., Stillwater, MN (US)

( * ) Notice: Subject to any disclaimer, the term of this patent is extended or adjusted under 35 U.S.C. 154(b) by 195 days.

(21) Appl. No.: 10/041,951

(22) Filed: Oct. 24, 2001

(65) Prior Publication Data

US 2002/0116013 A1 Aug. 22, 2002

Related U.S. Application Data (60) Provisional application No. 60/242,841, filed on Oct. 24, 2000.

(51) Int. Cl.$^7$ ............................................... A61B 17/56
(52) U.S. Cl. ........................... 606/74; 606/73; 606/103; 24/135 R
(58) Field of Search .............................. 606/60, 65, 72, 606/73, 74, 103, 201, 203, 232; 24/135 R, 136 R, 136 B, 163 R, 168, 115 R, 278, 481, 484, 20 LS (56) References Cited

U.S. PATENT DOCUMENTS

| | | | |
|---|---|---|---|
| 2,716,226 A | 8/1955 | Jonas | |
| 4,413,110 A | 11/1983 | Kavesh et al. | |
| 4,708,132 A | 11/1987 | Silvestrini | |
| 4,966,600 A | 10/1990 | Songer et al. | |
| 5,456,722 A | 10/1995 | McLeod et al. | ............... 623/13 |
| 5,628,756 A | 5/1997 | Barker, Jr. et al. | |
| 5,628,766 A | 5/1997 | Johnson | ....................... 606/232 |
| 6,053,921 A | 4/2000 | Wagner et al. | |
| 6,099,527 A | 8/2000 | Hochschuler et al. | .......... 606/61 |
| 6,214,007 B1 | 4/2001 | Anderson | ..................... 606/73 |

FOREIGN PATENT DOCUMENTS

EP  0 596 829 A1  5/1994

OTHER PUBLICATIONS

Spinal Concepts—Catalog #199–0001–MKC Rev B per DCR #284 Oct. 1998.

Now You See It. Now You Don't—SecureStrand, undated.

Instrumentation, Technique, and Technology—Neurosurgery, vol. 38, No. 4, Apr. 1996.

The Use of Sublaminar Cables to Replace Luque Wires—Richards Manufacturing Co., titanium cable system, undated.

Segmental Spinal Instrumentation with Spinous Process Wires, undated.

Tension Band Wiring–Bone Grafting for Spondylolysis and Spondylolisthesis, A Clinical and Biomechanical Study, undated.

Interspinous Process Segmental Spinal Instrumentation—J Pediatr Orthop, vol 4, No. 4, 1984.

Laminectomy with Posterior Wiring and Fusion for Cervical Ossification of the Posterior Longitudinal Ligament, Spondylosis, Ossification of the Yellow Ligament, Stenosis, and Instability: A Study of 5 Patients—J Spinal Disord. vol. 12, No. 6, 1999.

Modified Technique of Tension Band Wiring in Flexion Injuries of the Middle and Lower Cervical Spine, undated.

Posterior Wiring Without Bony Fusion in Traumatic Distracti ve Flexion Injuries of the Mid to Lower Cervical Spine—Long Term Follow–Up in 30 Patients, undated.

(List continued on next page.)

*Primary Examiner*—David O. Reip
(74) *Attorney, Agent, or Firm*—Vidas, Arrett & Steinkraus PA (57) ABSTRACT

A clip for holding two ends of a flat surgical cable includes an outer portion with female threads and an inner male portion having mating male threads.

15 Claims, 6 Drawing Sheets

OTHER PUBLICATIONS

Atlas Cable Systems—LIT.ATL.SS95 REV.B 2/99, undated.

Biomechanical Results—Biamechanical Testing Results of Posterior Spinal Cable Fixation Systems, undated.

Posterior Cervical Arthrodesis Using the Songer Cable System—Copyright 1996 by McGraw–Hill, Inc.

The Role of Cables in Lumbosacral Fusion—Reprinted from Lumbosacral and Spinopelvic Fixation Copyright 1996 by Lippincott–Raven Publishers.

Comparative Mechanical Properties of Spinal Cable and Wire Fixation Systems—SPINE vol. 22, No. 6, pp 596–604, 1997, Lippincott–Raven Publishers.

A Biomechanical Evaluation of Magnetic Resonance Imaging–Compatible Wire Cervical Spine Fixation SPINE vol. 18, No. 14, pp 1991–1994, Copyright 1993, J. B. Lippincott Company.

An In Vitro Study of the Biomechanical Effects of Flexible Stabilization on the Lumbar Spine SPINE vol. 22, No. 2, pp 151–155, Copyright 1997, Lippincott–Raven Publishers.

In Vitro Biomechanical Comparison of Multistrand Cables With Conventional Cervical Stabilization SPINE vol. 21, No. 18, pp 2108–2114, Copyright 1996, Lippincott–Raven Publishers.

TENSION BAND CLIP

CROSS-REFERENCE TO RELATED APPLICATIONS

This application claims priority from U.S. provisional application 60/242,841 filed Oct. 24, 2000, the entirety of which is incorporated herein by reference.

STATEMENT REGARDING FEDERALLY SPONSORED RESEARCH OR DEVELOPMENT

Not Applicable.

BACKGROUND OF THE INVENTION

This invention relates to a device for securing a cable, especially surgical cables.

Surgical procedures for the repair or fusion of large and small bones, ligaments and tendons, and other orthopedic procedures frequently require use of an orthotic device or attachment apparatus which can be subject to tensioning and bear heavy loads caused by the unique anatomical features of the compromised bone or tendon. For example, fractures of the patella are exposed to high stresses during flexion and extension of the knee joint; fusions of the spinal vertebrae are exposed to high gravitational forces and movements of the spinal column; torn ligaments and tendons are exposed to high stresses due to contraction of the associated muscle or flexion and extension of the bony structures; and trochanteric reattachment and cerclage techniques involve cable that is tensioned and exposed to high weight loads and stress factors.

Examples of surgical cable attachments include U.S. Pat. No. 4,966,600 to Songer et al. Clamps for holding the cables are shown in U.S. Pat. No. 6,053,921 to Wagner et al. A polyethylene cable system is described in U.S. Pat. No. 5,456,722 to McLeod et al. Polyethylene cable tying is shown in U.S. Pat. No. 5,628,756 to Barker Jr., et al.

U.S. Pat. No. 6,214,007 to Anderson shows a fastener where soft tissue grafts are fixed in place by a screw whose threads are affixed to bone and whose head together with a collar trap the graft therebetween. The screw is threaded into bone.

The art described in this section is not intended to constitute an admission that any patent, publication or other information referred to herein is "prior art" with respect to this invention, unless specifically designated as such. In addition, this section should not be construed to mean that a search has been made or that no other pertinent information as defined in 37 C.F.R. §1.56(a) exists.

BRIEF SUMMARY OF THE INVENTION

The invention provides a clip designed to grip and hold a tension band or cable without the use of any additional securing features such as knots. It is especially well suited for use with braided polyethylene cable. It employs a tapered screw concept which is customized using radii at both the root and crest of the thread. This prevents cutting of the cable. Standard clip designs using sharp teeth would cut individual cable strands leading to cable failure.

The cable design allows for easy engagement (starting of the thread) with progressively more compression of the braided cable. The female thread of the outer body is designed with a large radius where the cable exits to form a loop. All exiting edges are radiused. The thread profile follows the main taper and thus blends gradually to zero depth. This, along with the large exit radius, minimizes all sharp bends which act to cut the cable under cyclic loading.

BRIEF DESCRIPTION OF THE DRAWINGS

A detailed description of the invention is hereafter described with specific reference being made to the drawings in which.

DETAILED DESCRIPTION OF THE INVENTION

As described in U.S. Pat. Nos. 5,628,756 and 5,456,722, the disclosures of which are incorporated herein by reference, a suitable cable for surgical repair of bones, ligaments and tendons is a polyethylene braid. Commercial embodiments of the polyethylene fibers described in Kavesh et al., U.S. Pat. No. 4,413,110 are known by the trademarks SPECTRA-900 and SPECTRA-1000 and are sold by Allied-Signal, Inc. These commercially available fibers have a tensile strength of about 375,000–425,000 psi per individual monofilament. The density of each monofilament is between 0.5 and 1.5 g/cc, preferably about 0.97. Fibers of SPECTRA-1000 have a tenacity of approximately 35 g/denier, a specific gravity of 0.97 and an average diameter of 27 microns (0.0011 inch). Each monofilament is less than 100 microns in diameter. Fibers are assembled to form a tight weave which discourages fibrous ingrowth. Preferably, pore sizes are less than 30 microns. For ultra-high molecular weight polyethylene (UHMWPE), the cable 10 is optimally formed of 8 strands, each strand having from one to six ply. Each single ply strand contains approximately 120 fibers of UHMWPE. Thus, a braided load-bearing cable may have from 960 individual fibers for a one ply braid to 1920 individual fibers for a two ply braid. The cable 10 in the Figures may be such a cable or similar braided construction.

Such cables are very strong, but can be difficult to secure without compromising either the cable itself or the ability to place the securement where desired without loosening.

The load bearing cable may be utilized in a variety of surgical procedures to fuse or repair small bones and ligaments and tendons. For example, the cable may be used as an orthosis and shield the torn ligament or tendon from the normal stress and strain until the tissue has healed, e.g. by sewing the cable through remnants of a ligament and bringing the torn ends into opposition.

Alternatively, the cable may be used to shield normal stress and strain until the tissue has become strong enough to carry the full amount of stress, e.g. by securing the cable through a replacement tissue graft. The load bearing cable may be substituted for surgical wire or cable in the repair of small bone fractures such as the patella or bone fusions such as vertebral fusions. The cable has sufficient tensile strength to maintain bone fragments in close approximation to promote active healing and is sufficiently inelastic to prevent separation of fragments under tensile loading. The load bearing cable is less susceptible to fatigue failure than surgical wire. In the event the cable does fail, no threat of damage to surrounding tissue is posed.

Rather than trying to tie the ends of the cable 10 together as in U.S. Pat. No. 5,628,756, the present invention employs a novel clip 12 which consists of a male portion 14 and a female portion 16. As shown in the figures, the clip employs a tapered screw concept.

The female thread 18 of the outer female portion 16 is formed with a large radius 20 where the cable 10 would exit to form a loop. The thread profile follows a main taper 22 and gradually blends to zero depth as it exits the large radius 20, all exiting edges are substantially radiused. The substantial radius eliminates the relative sharpness of the roots/valleys and crests/peaks. The male screw portion 14 has a root/valley radius 24, a crest/peak radius 26 along the length of the part and each end has radii 28 and 30.

Figures 1, 2, 3, 4:
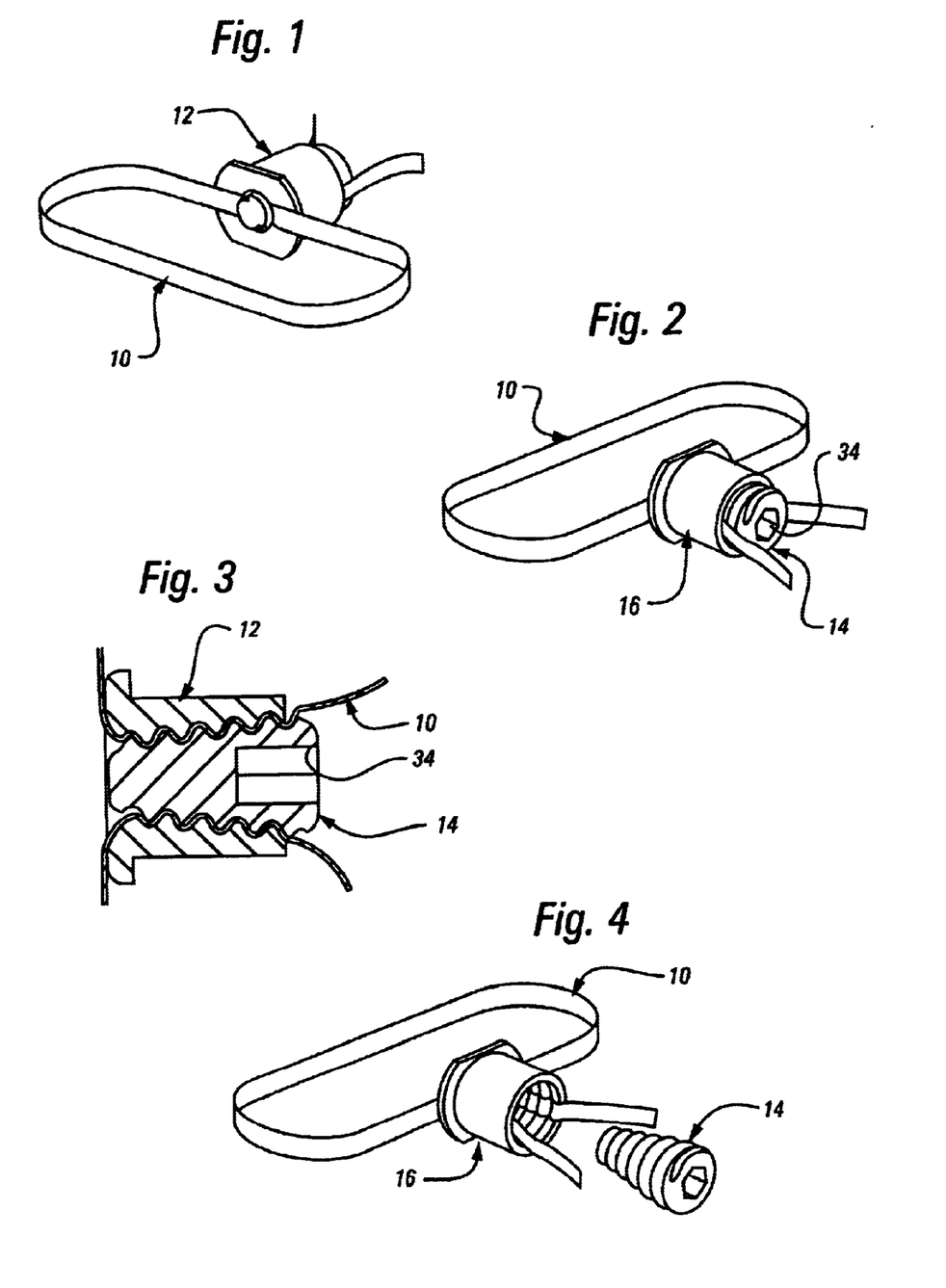
FIG. 1 is a perspective view of the clip showing a braided polymeric cable secured thereto.
FIG. 2 is a perspective view of the clip showing a braided polymeric cable secured thereto.
FIG. 3 is a cross-sectional view of the clip showing the cable secured thereto.
FIG. 4 is a perspective view of the clip of FIG. 2 with the male porion of the clip unscrewed.
Figure 5:
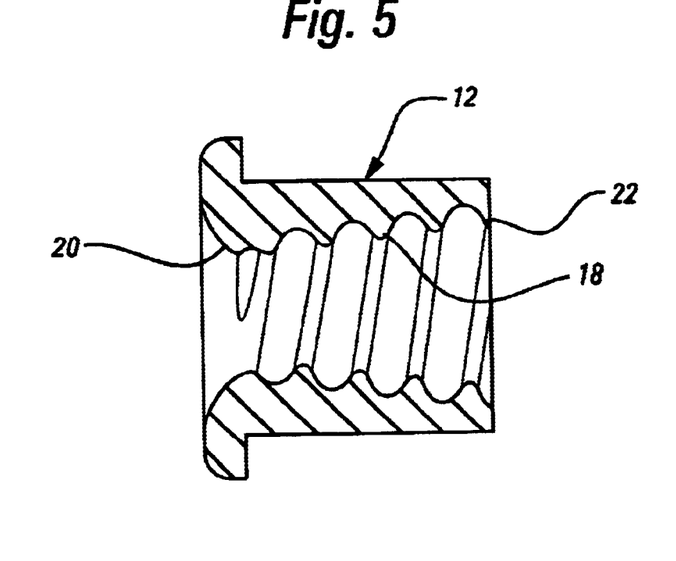
FIG. 5 is a cross-sectional view through the female portion of the clip.
Figure 6:
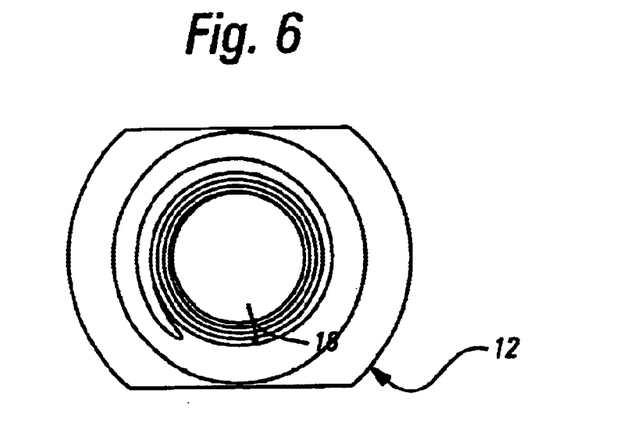
FIG. 6 is a top view of the female portion of the clip.
Figure 7:
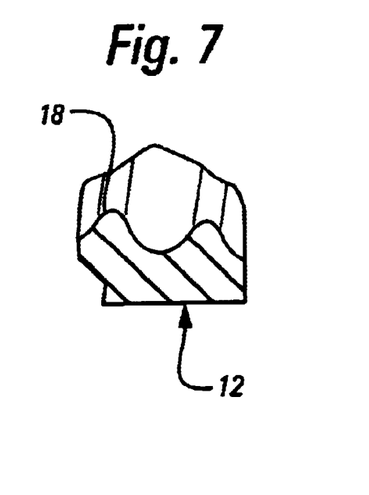
FIG. 7 is a enlarged cross-sectional view of the threads of the female portion of the clip.
Figure 8:
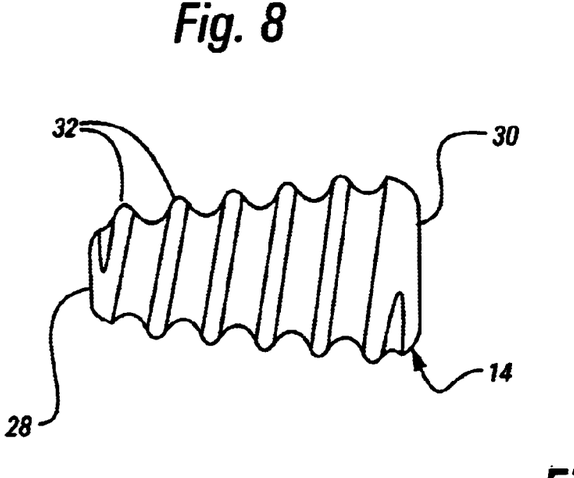
FIG. 8 is a side view of the male portion of the clip.
Figure 9:
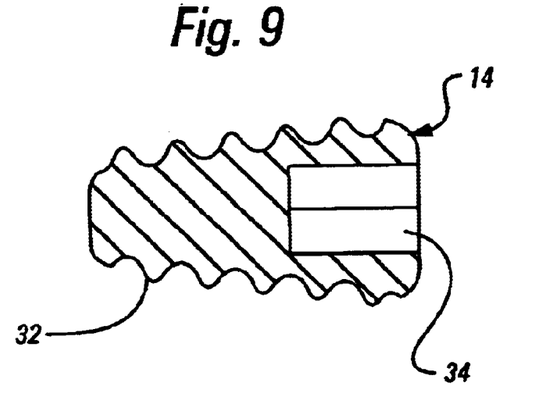
FIG. 9 is a cross-sectional view of the male portion of the clip.
Figure 10:
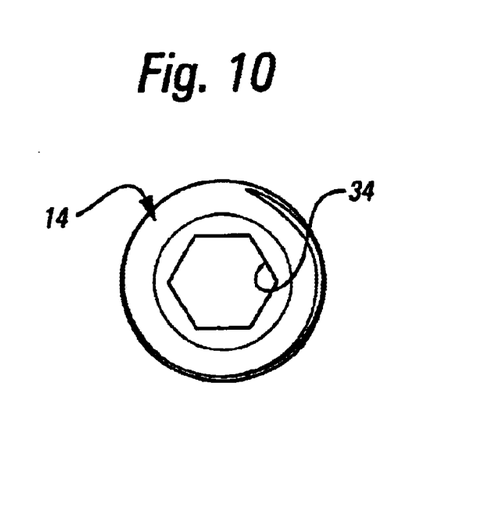
FIG. 10 is a top view of the male portion of the clip.

By way of example only, as shown in FIG. 7, the threads 18 may have a height of about 0.025 inches (0.635 mm) and a radius of 0.010 inches (0.254 mm) at the peak and 0.021 inches (0.533 mm) at the troughs. The taper may be at an angle of about 10° and the threads may have a 0.065 inch (1.65 mm) pitch. A typical width of the female portion across the narrowest top portion of FIG. 6 may quite small, for example 0.312 inches (0.792 cm).

In the example above, the male thread 32 would have a similar thread height and radius at the peak and troughs, a taper at about 10° and an end radius at the distal end of about 0.050 inches (1.27 mm). The male portion 14 also includes a mechanism 34 which allows the male portion to be threaded in and out of the female portion 16. As shown, the mechanism 34 is a simple female hex head, however, any of the known end techniques for imparting rotational force to a screw may be employed.

Figure 11:
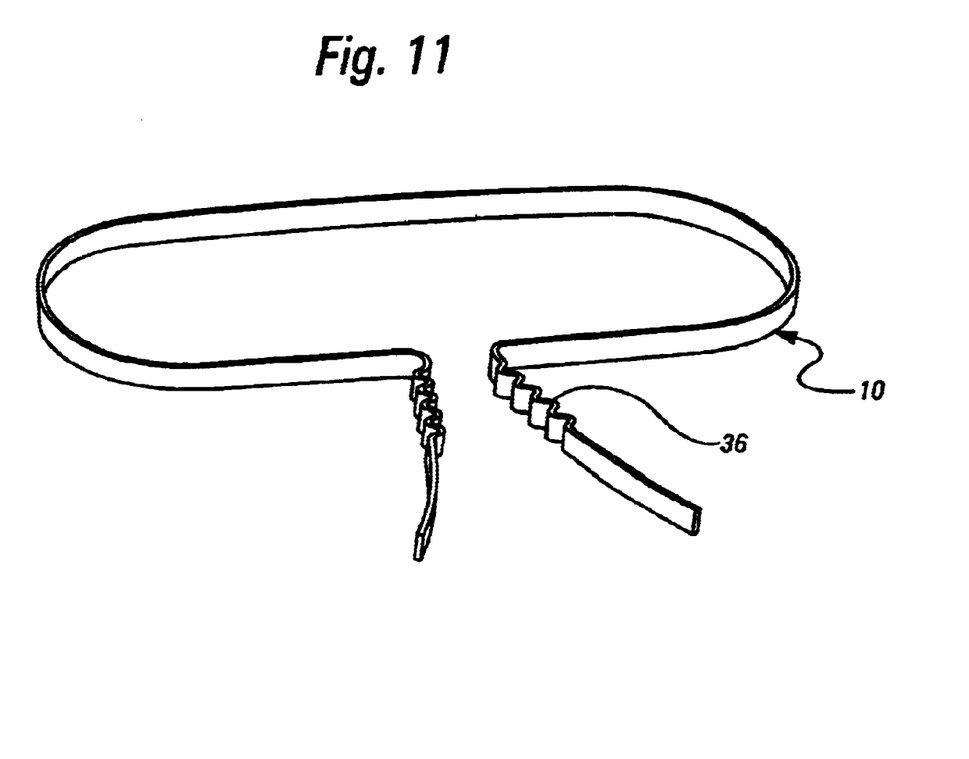
FIG. 11 is a perspective view of a cable after the clip has been released.
Figure 12:
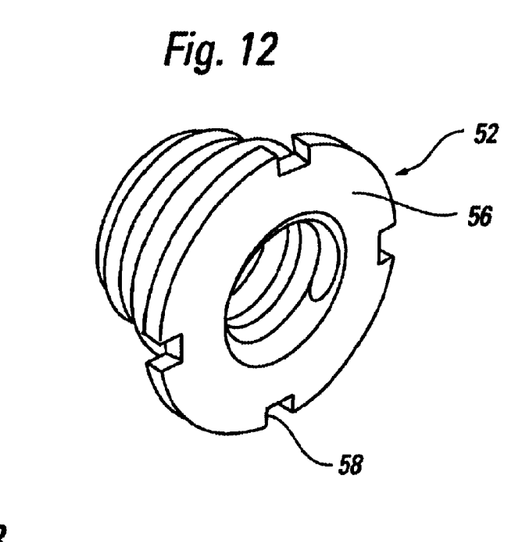
FIG. 12 is a perspective view of the proximal end of an alternative female portion having external threads.
Figure 13:
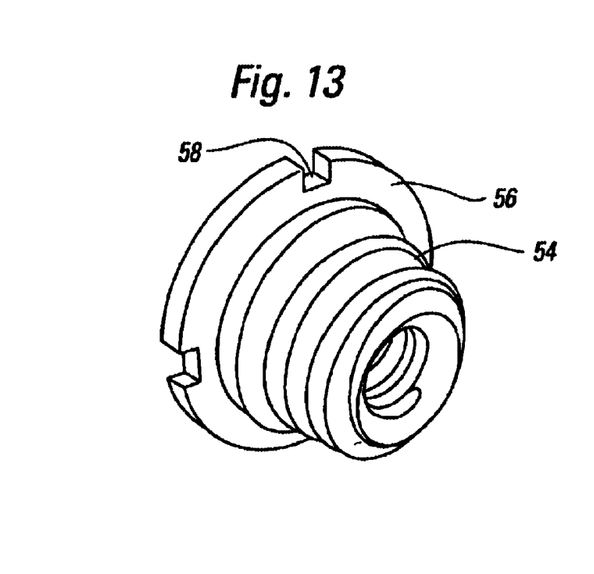
FIG. 13 is a perspective view of the alternative female portion showing the distal end.
Figure 14:
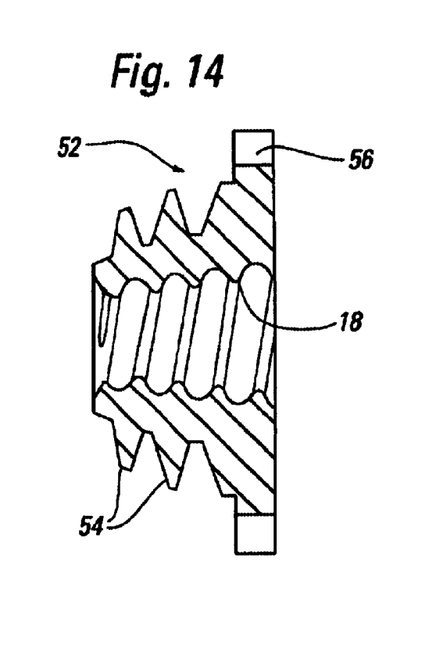
FIG. 14 shows a cross-sectional view through the alternate female portion.
Figure 15:
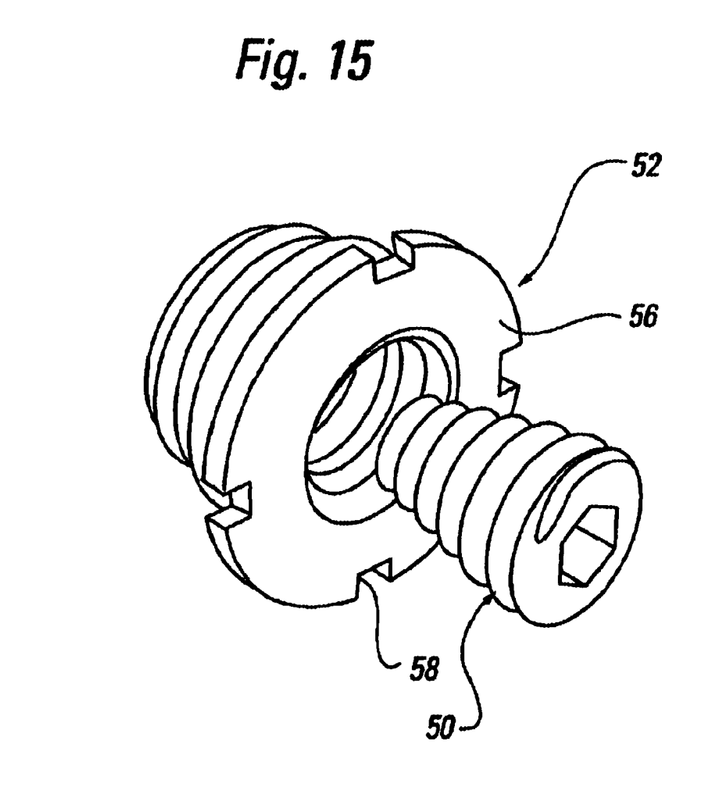
FIG. 15 shows the alternate female portion about to engage with a male portion.
Figure 16:
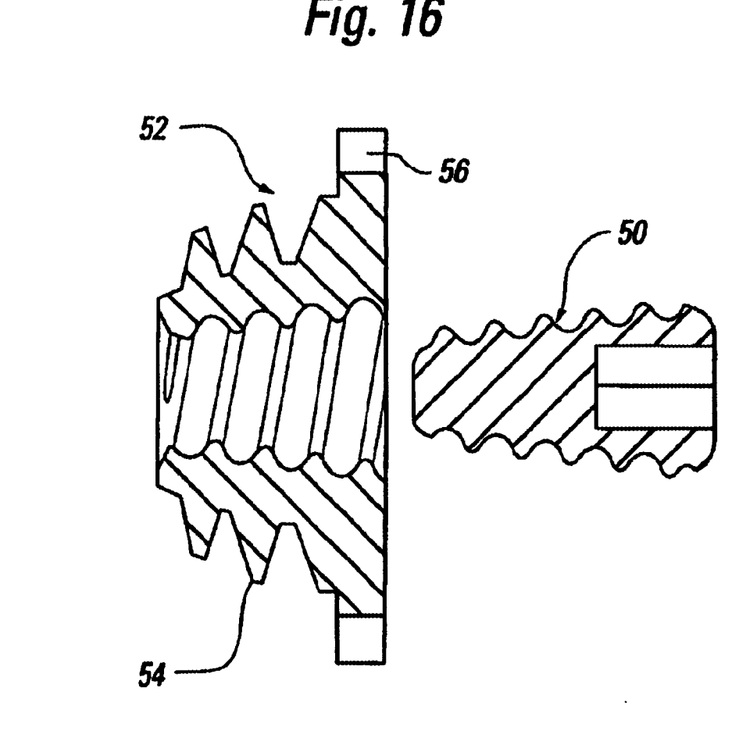
FIG. 16 shows a cross-sectional view of the alternate female portion and the male portion aligned for engagement.

As shown in the figures and especially in FIG. 11, a cable 10 which has been secured in the clip 12 of the invention is held firmly throughout the length of the threads, causing a large compressive force to be applied throughout a long section of the cable, to minimize any stress and weakening of the cable. The bights 36 in the cable 10 show the engagement. Conventional threads would have sharp edges that would cut the cable under cyclic loading. Tests have shown that the inventive clip provides exceptional strength and holding while minimizing degradation of the cable.

FIGS. 12–16 show an alternative form of the clip 60 in which the male portion 50 is basically the same, but the female portion 52 includes external threads 54 and a head 56 with slots 58 or other mechanism for holding and driving the female portion 52 into a body region, such as in the repair of an anterior cruciate ligament. The exterior surface of the female portion 52 may include threads 54, knurling or any other surface treatment that promotes engagement of the portion with bone. When threaded, the outer surface may be tapered.

Pull-out resistance is achieved by a combination of compressive force placed on the cable and the multiple changes in direction (bends) of the cable that the clip imparts on the cable.

While this invention may be embodied in many different forms, there are shown in the drawings and described in detail herein specific preferred embodiments of the invention. The present disclosure is an exemplification of the principles of the invention and is not intended to limit the invention to the particular embodiments illustrated.

This completes the description of the preferred and alternate embodiments of the invention. Those skilled in the art may recognize other equivalents to the specific embodiment described herein which equivalents are intended to be encompassed by the claims attached hereto.

What is claimed is:

1. A surgical fastener for use in fastening cable, said fastener comprising:
    a) a female portion having a body defining an opening between a proximal and a distal end, said opening being threaded and tapering from a largest diameter at the proximal end to the distal end, said distal end including a radius against which cable may be placed; and
    b) a male portion constructed and arranged to mate with said female portion, said male portion having a proximal and a distal end, with threads therebetween and radii at the crest and root of said threads, said proximal end including a mechanism by which external rotational force may be applied to said male portion to turn said male portion in and out of said female portion.

2. The surgical fastener of claim 1 wherein said mechanism at said proximal end of said male portion is a hex head.

3. The surgical fastener of claim 1 wherein said threads of said male and female portion are tapered at an angle of about 10°.

4. The surgical fastener of claim 3 wherein said male and female threads have similar radii when threaded together to maximize holding power and minimize cable stress points when a cable is held therebetween.

5. The surgical fastener of claim 1 wherein said threads incorporate a substantial radius at the root and crest.

6. The surgical fastener of claim 1 wherein said threads at said distal end of said female portion have a substantial exit radius.

7. The surgical fastener of claim 1 wherein the body of said female portion includes an outer surface treatment constructed and arranged for bone engagement.

8. The surgical fastener of claim 7 wherein the outer surface of the female portion is tapered.

9. The surgical fastener of claim 7 wherein the outer surface of the female portion is threaded or knurled.

10. A surgical fastener system comprising:
    a) a female portion having a body defining an opening between a proximal and a distal end, said opening being threaded and tapering from a largest diameter at the proximal end to the distal end, said distal end including a radius against which cable may be placed;
    b) a male portion constructed and arranged to mate with said female portion, said male portion having a proximal and a distal end, with threads therebetween and radii at the crest and root of said threads, said proximal end including a mechanism by which external rotational force may be applied to said male portion to turn said male portion in and out of said female portion; and c) a cable.

11. The surgical fastener system of claim 10 wherein said cable has two ends and a flat braided polyethylene cable.

12. The surgical fastener system of claim 11 wherein said cable is formed from ultra-high molecular weight polyethylene.

13. A surgical fastener for securing a cable therewithin, the fastener comprising:

a) a female portion having an opening therethrough between a top and a bottom of said female portion, said opening tapering from a largest diameter at the top and a smaller diameter at the bottom end, said opening being threaded;

b) a male portion having a top and a bottom portion and external threads therebetween, said male portion being constructed and arranged to taper at the same angle as the taper of the female portion opening and having threads constructed and arranged to mate with said female portion threads when said male portion is threaded into said opening of said female portion, each of the threads of said male and female portion being radiused to lower stress and weakening of a cable inserted between said threads prior to tightening of said male portion into said female portion.

14. The surgical fastener of claim 13 wherein said male portion includes a mechanism at its top through which external rotational force may be applied.

15. The surgical fastener of claim 14 wherein said mechanism is a female shaped opening to fit a male driver having a mating head.

* * * * *